United States Patent
Kolaja et al.

(10) Patent No.: US 6,840,085 B1
(45) Date of Patent: Jan. 11, 2005

(54) PHOTOIONIZATION DETECTOR WITH MULTIPLE IONIZATION CELLS

(76) Inventors: Robert J. Kolaja, 84 Engsleigh Cresc., Toronto, Ontario (CA), M2J 3N9; Nicholas J. Barker, 412 Royal Oak Rd. RR#1, Manilla, Ontario (CA), K0M 2J0; Ori D. Raubvogel, 105 Downing Blvd., Thornhill, Ontario (CA), L4J 7N5

( * ) Notice: Subject to any disclaimer, the term of this patent is extended or adjusted under 35 U.S.C. 154(b) by 196 days.

(21) Appl. No.: 10/242,193

(22) Filed: Sep. 11, 2002

Related U.S. Application Data

(60) Provisional application No. 60/322,778, filed on Sep. 18, 2001.

(51) Int. Cl.[7] ............................ G01N 30/00; G01N 7/00
(52) U.S. Cl. .................... 73/23.37; 73/28.02; 73/31.01; 250/374
(58) Field of Search ............................ 73/23.37, 28.02, 73/30.01, 31.02, 31.03; 250/374

(56) References Cited

U.S. PATENT DOCUMENTS

| | | | |
|---|---|---|---|
| 3,057,376 A | | 10/1962 | Agutter et al. |
| 3,355,587 A | * | 11/1967 | Jenckel .................. 73/23.37 |
| 4,353,243 A | | 10/1982 | Martin |
| 4,398,152 A | | 8/1983 | Leveson |
| 4,429,228 A | * | 1/1984 | Anderson .................. 250/374 |
| RE33,415 E | * | 10/1990 | Jelic .......................... 313/609 |
| 5,083,742 A | | 1/1992 | Wylie et al. |
| 5,561,344 A | * | 10/1996 | Hsi ............................ 313/494 |
| 5,594,346 A | * | 1/1997 | Stearns et al. ............. 324/464 |
| 6,320,388 B1 | * | 11/2001 | Sun et al. ................... 324/464 |
| 6,333,632 B1 | * | 12/2001 | Yang et al. ................. 324/464 |
| 6,509,562 B1 | * | 1/2003 | Yang et al. ................. 250/287 |
| 6,734,435 B2 | * | 5/2004 | Sun et al. ................ 250/423 P |

* cited by examiner

Primary Examiner—Michael Cygan

(57) ABSTRACT

A photoionization detector comprising multiple ionization cells for detecting the presence of chemical compounds in multiple fluid samples. The photoionization detector uses a single source of ultraviolet (UV) radiation to emit high energy photons into at least two ionization cells. Each ionization cell comprises at least one fluid inlet and at least one fluid outlet. Independent samples of fluid can be introduced into each cell and exposed to the UV radiation such that any molecules with an ionization energy lower that the energy of the photons are ionized. Each ionization cell also comprises a set of at least two electrodes arranged to generate an electric field such that ionized molecules are attracted to the electrode at lower voltage potential resulting in an electrical current.

13 Claims, 2 Drawing Sheets

PHOTOIONIZATION DETECTOR WITH MULTIPLE IONIZATION CELLS

CROSS-REFERENCE TO RELATED APPLICATION

This application claims priority from U.S. provisional patent application Ser. No. 60/322,778, for Photoionization Detector With Multiple Ionization Cells, filed Sep. 18, 2001, the disclosure of which is incorporated herein by reference.

BACKGROUND OF THE INVENTION

1. Field of the Invention

The present invention is related to photoionization detectors for detecting the presence of chemical compounds in a fluid and more particularly to a photoionization detector that comprises multiple ionization cells.

2. Description of the Background Art

Photoionization detectors (PIDs) are conventionally used to detect the presence of chemical compounds in air. When a molecule is exposed to high-energy photons of the appropriate photon energy, the molecule will become ionized. A pair of electrodes are arranged to be exposed to the ionized molecule such that the electrodes are electrically insulated from each other and are maintained at a voltage differential from each other. The ion is repelled from the higher voltage electrode and attracted to the lower voltage electrode. When a fluid stream is exposed to the high-energy photons, and a number of ions are produced, a measurable current is generated.

Conventionally, a PID that is used in an instrument for the purpose of detecting chemical compounds in air includes; an ultraviolet (UV) radiation source as a source for high energy photons and associated electronic circuitry for driving the UV radiation source; an ionization cell into which the output of the UV radiation source is directed, a means for a sample of gas to enter and exit the ionization cell; and two or more electrodes electrically insulated from each other and held at a voltage differential and associated electronic circuitry to maintain the voltage differential, the electrodes having a size, shape, and orientation to effectively produce a current when exposed to ions.

In a classical PID design, a glass discharge UV lamp is used to produce high-energy photons. Typically, the lamp is constructed of a sealed glass volume filled with a gas such as helium, argon, krypton, or xenon with a window made from a material that is highly transmissive of UV radiation such as magnesium fluoride, lithium fluoride, barium fluoride, strontium fluoride, calcium fluoride or sapphire and the glass volume also contains two electrodes. By maintaining the electrodes at a voltage differential, the gas in the glass volume is momentarily excited. The excited gas then returns to the ground state and in doing so emits photons. U.S. Pat. No. 4,398,152 to Leveson describes a gas discharge UV lamp that eliminates the need for electrodes in the glass volume and excites the gas in the glass volume by inductively coupled radio frequency and produced UV radiation that is uniform across the cross-section of the UV lamp. The glass volume is placed in a holder made of polytetrafluoroethylene around which a coupling inductor is wound and connected at one end to an oscillator circuit to generate radio frequency.

The electrodes can have a variety of designs, including, a concentric format with one electrode in the middle of a cylindrically shaped electrode, two disc shaped electrodes in parallel spaced apart with an electric insulator, two thin rods oriented in parallel. The electrodes must be spaced appropriately. Improperly spaced electrodes, either too closely spaced or too widely spaced, will have a negative impact on the overall sensitivity of the detector. Specifically, in the case of too closely spaced electrodes, the electric field is smaller and fewer ions are exposed to the electric field; in the case of too widely spaced electrodes, ions have a greater chance of colliding with a free electron and recombining and the electric field is weaker and would not as strongly attract the ions.

Typically PIDs are designed with small internal volumes and volumes that are continually swept with gas to achieve good analytical performance. Unduly large internal volumes allow the sample to diffuse and generate results that are less accurate. Volumes that are poorly swept, such as holes or tubes that have no exit, or unnecessary changes in cross-sectional areas of the flowpath also allow the sample to diffuse and can allow the sample to reside in the poorly swept volume even after an analysis is complete, and such residual sample can then contaminate a subsequent analysis.

Typically PIDs are made from materials that have high chemical inertness so as to minimize the interaction of the PID with the sample and potentially contaminate the sample and to minimize adsorption of gas into the material to be potentially later released into subsequent analyses.

The sample can be introduced into the ionization cell in a number of ways, including for example: by placing a pump downstream of the PID, the vacuum generated by the pump causing gas to flow through the PID in which case the PID is somewhat evacuated; by placing a pump upstream of the PID, the pressure generated by the output of the pump causing gas to flow through the PID in which case the PID is somewhat pressurized; an injection of sample into the PID by syringe or other means; by injection of the sample into a carrier gas flow stream and passing the sample and carrier gas through a chromatographic column and then through the PID in which case the ionization cell is somewhat pressurized.

In any case, care must be taken to adequately seal the PID from its ambient environment so as not to unduly allow sample or carrier gas to leak out of the PID prior to ionization in the case of a pressurized system, and so as not to allow gases from the ambient environment to be introduced into the ionization cell and potentially contaminate the sample in the ionization cell.

A PID alone typically cannot provide a user with information to distinguish the specific molecules and concentrations of a number of types of molecules that are in a sample. The UV source will emit photons of a specific energy and any molecules that have an ionization energy lower than the energy of the photons will become ionized. If there is a single type of molecule present in the sample that has an ionization energy lower than the energy of the photon, a current will be generated and if compared against a known reference of the same type of molecule, a concentration of the molecule in the sample can be determined. However, if there is more than one type of molecule that is thus ionized, the user will be unable to discern the molecules that are present, the concentrations that are present, nor the number of different types of molecules present.

This drawback of PIDs is typically addressed by passing the fluid to be measured through a chromatographic column prior to introduction into the ionization cell. The various chemical compounds that are in the fluid will be separated from each other in the chromatographic column and will be introduced into the PID individually. The concentrations of each individual chemical compound can then be measured, and in many cases the chemical compounds can be identified based on the timing at which the chemical compounds are eluted from the chromatographic column.

Though it is advantageous to use a chromatographic column to introduce a fluid to the PID, there is a significant delay between the time a fluid sample is collected and the time the various chemical compounds are eluted from the chromatographic column to be measured by the PID. Conversely, if no chromatographic column is used, there is relatively no delay between the time a fluid sample is collected and the time it is introduced into the PID. There exists many applications that require a specific analysis that identifies and quantifies the chemicals in a fluid sample and there exists many applications that require minimal time delay. Also, analyses that require identification and quantification of the chemical compounds tend to also require the measurement of very low concentrations of the chemical compounds and thus require greater sensitivity of the detector. Analyses that require minimal time delay and do not require identification and quantification of chemical compounds often require the measurement of relatively high concentrations of the chemical compounds and thus require a detector capable of measuring a broad range of concentrations of chemical compounds. Though it is advantageous for a chemical compound detection instrument to allow for both types of operation, existing PIDs cannot reconcile the conflicting requirements of the variety of applications.

SUMMARY OF THE INVENTION

The present invention improves on existing photoionization detectors (PID) by arranging multiple ionization cells to be exposed to a single source of high energy photons. The ionization cells are arranged such that each ionization cell can receive an independent fluid stream, allow for molecules in the fluid stream of each ionization cell to be ionized, and generate a current in each cell by the presence of a set of electrodes maintained at a voltage differential.

An ultraviolet radiation source is used as the source of high energy photons and the UV radiation is arranged to pass into a series of ionization cells, in which any ionizable compounds are ionized. The sequence of ionization cells can be continued so long as the intensity of the UV radiation remains sufficient to produce a measurable number of ions. The ionization cells each have at least one inlet and at least one outlet through which fluids may enter and exit the cells. The fluids in the respective ionization cells are substantially prevented from contacting each other and potentially contaminating each other and the cells are substantially sealed from the ambient environment.

Each ionization cell has a set of at least two electrodes that are maintained at a high voltage potential to attract the ions to the electrode at the lower voltage potential and produce a measurable current. The electrodes are spaced appropriately to be exposed to a large portion of the ionized molecules and are close together to be exposed to the ionized molecules before they recombine.

DETAILED DESCRIPTION OF THE PREFERRED EMBODIMENTS

Figure 1:
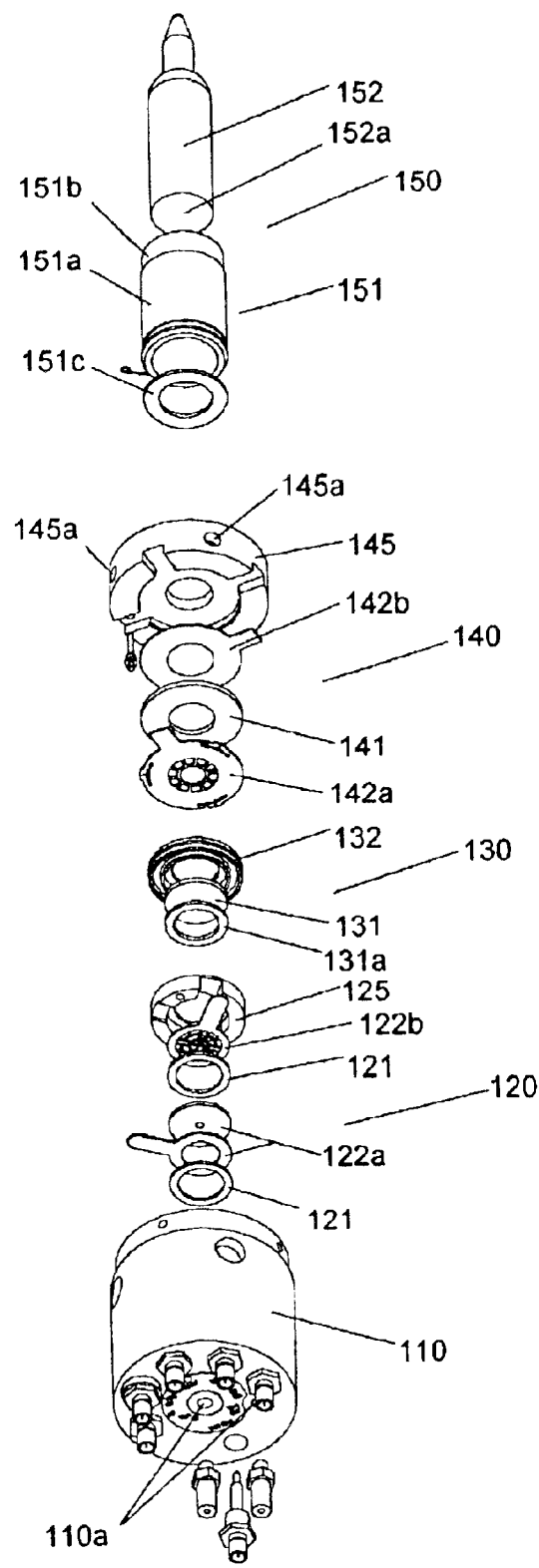
FIG. 1 is an exploded view of one embodiment of a photoionization detector with two ionization cells in accordance with this invention.
Figure 2:
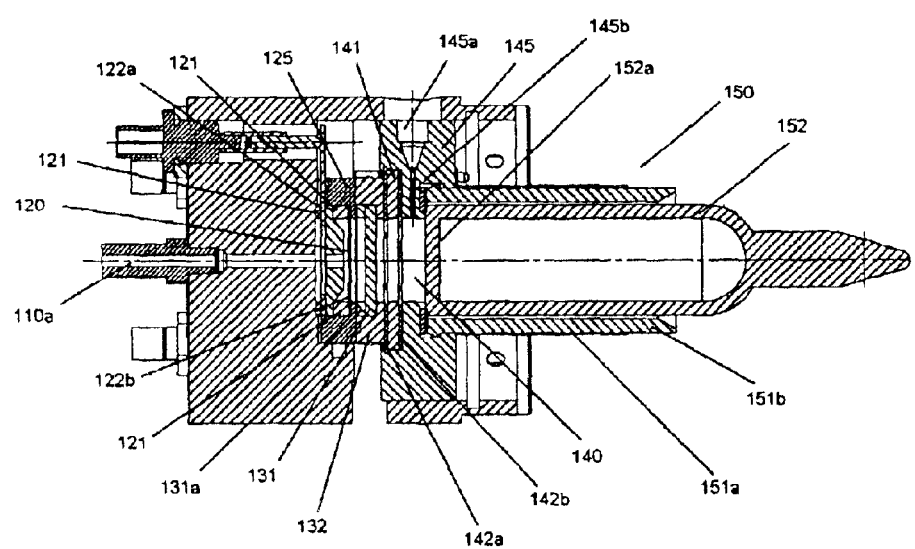
FIG. 2 is a cross-sectional view of the construction of one embodiment of a photoionization detector with two ionization cells in accordance with this invention.

FIG. 1 shows an exploded view and FIG. 2 shows a sectional view of a photoionization detector in accordance with an embodiment of this invention. Detector housing 110 holds a first ionization cell 140, a window assembly 130, a second ionization cell 120, and an ultraviolet (UV) radiation source 150.

In one embodiment, UV radiation is generated by a UV lamp 152. The UV lamp body is made of glass and is filled with krypton, argon, xenon, or helium and a UV lamp window 152a on the end of the lamp, the UV lamp window 152a made of a material that is transmissive of UV radiation such as magnesium fluoride, lithium fluoride, barium fluoride, strontium fluoride, calcium fluoride or sapphire. The lamp is placed in a radio frequency (RF) inductive coupler 151 that is comprised of a RF holder 151b made of polytetrafluoroethylene (PTFE) and an inductive coupler coil 151a wound around the RF holder 151b, the inductive coupler coil 151a being connected at one end to an RF oscillator circuit. Excitation of the gas in the UV lamp 152 by the RF field generates UV radiation which propagates into a first ionization cell 140.

A fluid can be introduced into a first fluid port 145a of a first ionization cell housing 145. The fluid propagates along a passage 145b into the first ionization cell 140. Molecules in the fluid that have an ionization energy lower than the photon energy of the UV radiation source 150, will be ionized. The ionized molecules are exposed to an electric field generated by a first electrode 142a and a second electrode 142b which are maintained at a voltage differential and positioned an appropriate distance from each other, in one embodiment by an electrical insulator 141, such that an adequate portion of the ions reach the electrodes before they collide with a free electron and recombine. The ions are attracted to the electrode at lower voltage and result in a measurable current through the electrodes. The electrodes are electrically insulated from the detector housing 110, in one embodiment by the ionization cell housing 145 which is made from an electrically insulating material such as PTFE and in one embodiment is made from polyetheretherketone (PEEK). The gas exits the first ionization cell 140 through a second fluid port (not shown) in the first ionization housing 145.

The UV radiation propagates through the first ionization cell 140 and through a window assembly 130. In one embodiment, the window assembly 130 is comprised of a window retainer 132 that holds a window 131 and is held in place by a window clamping ring 131a. The window 131 is made of a material that is transmissive of UV radiation such as magnesium fluoride, lithium fluoride, barium fluoride, strontium fluoride, calcium fluoride or sapphire.

The UV radiation propagates into a second ionization cell 120. A fluid can be introduced into the second ionization cell 120 through a first fluid port 110a in the detector housing 110. The fluid propagates through a passage 110b into the second ionization cell 120. Molecules in the fluid that have an ionization energy lower than the photon energy of the UV radiation in the second ionization cell 120 will be ionized and exposed to an electric field generated by a first electrode 122a and a second electrode 122b which are maintained at a voltage differential and positioned an appropriate distance from each other, in one embodiment by an electrical insulator 121. The electrodes are electrically insulated from the detector housing 110 by an electrically insulating material such as PTFE or PEEK and in one embodiment, there is a second electrical insulator 121 made from PTFE between the first electrode 122a and the detector housing 110, and the ionization cell housing 125 is made from PEEK. The fluid exits the second ionization cell 120 through a second fluid port (not shown) in the detector housing 110. In some applications and in one embodiment it is beneficial for there to be a third electrode to reduce the effects of electrical leakage induced by contamination on the inside surfaces of the detector.

In one embodiment, there are a first and a second ionization cell. In other embodiments, there may be a second or more window assemblies through which the UV radiation may further propagate and a third or more ionization cells each with two electrodes and fluid inlet and outlet ports. In one embodiment, the number of ionization cells that can be arranged is limited by the intensity of the UV radiation in the more distant ionization cells, the intensity of UV radiation decreasing with distance from the UV radiation source. Also, each window and the fluid in each ionization cell absorb a portion of the UV radiation. If the ionization cells are arranged particularly close to the UV radiation source, a greater number of ionization cells may be viable. The spacing of the ionization cells is also determined by consideration of the spacing of the electrodes in each cell, closer spaced electrodes possibly allowing closer spaced ionization cells, and thus a greater number of ionization cells. Changing the spacing of the electrodes requires careful consideration of the resulting impact on the detector's sensitivity, because electrodes that are spaced closer than the optimal spacing results in fewer ions being exposed to the electric field and can be compensated for by a variety of means such as: increasing the voltage differential of the electrodes, increasing the intensity of the UV radiation.

Depending on the application, the components that are exposed to the fluids in question should be chemically inert such that the fluid is not contaminated by the components, and so that the components do not unduly adsorb molecules from the fluid and potentially contaminate fluids that enter the detector subsequently. In applications that require a very high degree of chemical inertness, materials such as special grades of stainless steel, glass, sapphire, nickel, or platinum should be used. Also, the degree of chemical inertness that is required may differ between the first ionization cell 140 and the second ionization cell 120, depending on the particular application for which each ionization cell is used. In one embodiment, the first ionization cell 140 receives a fluid that elutes from a chromatographic column and the second ionization cell 120 receives a fluid directly from the ambient environment. In this embodiment, a high degree of sensitivity to detect the presence of ionizable molecules of a few parts per billion is required of the first ionization cell 140 and wide range of sensitivity is required of the second ionization cell 120 but sensitivity is less important. In this embodiment, the components of the first ionization cell 140 are made from highly chemically inert materials, for example, the first ionization cell housing 145 is made from polyetheretherketone (PEEK), the electrical insulator 141 is made from PTFE, the window retaining ring is made from PEEK, and the electrodes are made from stainless steel. In this embodiment, the components of second ionization cell 120 are made from less highly chemically inert materials, for example, the detector housing which receives the fluid that is introduced into the second ionization cell is made from electroless nickel plated aluminum and fluid is transmitted through tubing made from fluorocarbon polymer (VITON), the electrodes made from stainless steel, the second ionization cell housing made from PEEK, and the electrical insulators made from PTFE.

Because the UV radiation intensity lessens with distance from the UV radiation source, fluids that are introduced into ionization cells that are more distant from the UV radiation source will ionize less readily than fluids introduced into ionization cells that are close to the UV radiation source. The respective cells into which fluids are introduced should be chosen with the UV radiation intensity in consideration. In one embodiment, the fluid that is introduced into the first ionization cell is more likely to have a low concentration of ionizable molecules, possible a few parts per billion and the fluid that is introduced into the second ionization cell is likely to have a wide range of concentrations of ionizable molecules and it is less important for a very low concentration of ionizable molecules to be readily detected.

It is desirable that the different fluids that enter the first ionization cell 140 and second ionization cell 120 do not unduly come into contact which each other and potentially contaminate each other. It is also desirable that the fluids in the respective ionization cells do not unduly leak to the ambient environment and potentially affect the sensitivity of the detector or that fluids from the ambient environment do not unduly leak into the respective ionization cells and potentially contaminate the fluids in the ionization cells. The extent to which the ionization cells must be thus sealed from the ambient environment and from each other depends on the specific application, but factors that must be considered include: the means by the fluid is propagated through the ionization cells and the resulting magnitude of the pressure or vacuum that results in the ionization cells, and the properties of the fluids that are in question and the concentration and types of molecules that are present in the fluids. In one embodiment, the fluids that are introduced into the first ionization cell 140 are propagated in a carrier gas and are passed through a chromatographic column and the first ionization cell 140 is thus somewhat pressurized. In this embodiment, the fluids that are introduced into the second ionization cell 120 are propagated by a pump that is positioned at the exit of the second ionization cell 120 and thus the second ionization cell is somewhat evacuated.

In any case, an adequate seal can be achieved by a variety of means including, for example, by producing highly smooth and flat surfaces on the various spacers, electrodes, and housings of the detector and applying a force on the arrangement to press the various components against each other to sufficiently block the flow of fluid between any two components; or by using seals such as gaskets and o-rings between components to effect a seal. In using seals, careful consideration of the materials from which the seals are made must be observed. Seals made from elastomers can adsorb the fluid in the ionization cells and potentially release the adsorbed fluids into subsequent analyses or potentially emit foreign contaminants into the fluid stream. Seals offer benefits of allowing less special attention being paid to the smoothness of the surfaces of the various components and potentially result in cost savings of the overall assembly. In one embodiment, the electrical insulator 141 has a groove (not shown) formed in either planar side to accept an elastomeric o-ring (not shown) and achieve a seal between the first electrode 142a and the electrical insulator 141 and the second electrode 142b and the electrical insulator 141. In one embodiment, the window retainer 132 has a groove (not shown) formed in either planar side to accept an elastomeric o-ring (not shown) and achieve a seal between the window retainer 132 and the second ionization cell housing 125 and the window retainer 132 and the electrode 142a. In one embodiment, a force is applied to the arrangement by pressing on the end of the lamp with a lamp retainer (not shown).

Depending on the application, the surfaces of the window 131 and the lamp window 152a can become contaminated and may require periodic cleaning or replacing. In one embodiment, the window retainer 132 is secured in a holder (not shown) that protrudes through a slot (not shown) in the detector housing 110, the holder being removable by the user, and the UV lamp is secured in a lamp retainer (not shown) that is removable by the user. In another embodiment, contamination of the window 131 and lamp window 152a occurs more slowly and are not made to be easily removable by the user.

The embodiments described above are illustrative and not limiting of the invention. Many additional and alternative embodiments will be apparent to those skilled in the art without departing from the essential characteristics of the invention as claimed below.

What is claimed is:

1. A photoionization detector, comprising:
   a plurality of ionization chambers arranged coaxially, each of the ionization chambers comprising at least one fluid inlet port, at least one fluid outlet port, and at lest two electrodes arranged to generate an electric field to attract positively charged particles to at least one of the electrodes;
   an ultraviolet (UV) lamp that generates UV radiation arranged to transmit UV radiation into each the ionization chambers; and
   at least one window, each window disposed between two of the ionization chambers, each window being transmissive of UV radiation.

2. The photoionization detector of claim 1, wherein the electrodes are arranged such that the at least one electrode to which positively charged particles are attracted is substantially not exposed to the transmitted UV radiation.

3. The photoionization detector of claim 1, wherein the UV lamp comprises:
   a sealed glass envelope filled with an inert gas, the sealed glass envelope having an ultra-violet (UV) transmissive window fixed to one end; and
   an electrically conductive coil, positioned substantially concentrically around the sealed glass envelope, the electrically conductive coil being connected to a radio frequency source tuned to excite the inert gas.

4. The photoionization detector of claim 1, wherein the at least one fluid inlet port and the at least one fluid outlet port are arranged such that the fluid propagates in a direction perpendicular to the direction of propagation of the UV radiation.

5. The photoionization detector of claim 1, wherein at least one window is made from a material selected from, the group consisting of:
   magnesium fluoride;
   lithium fluoride;
   barium fluoride;
   strontium fluoride;
   calcium fluoride; and
   sapphire.

6. The photoionization detector of claim 1, wherein at least one window is removable.

7. The photoionization detector of claim 1, wherein the number of ionization chambers is equal to two.

8. The photoionization detector of claim 7, wherein:
   the fluid inlet port of a first of the ionization chambers is connected to an outlet of a chromatographic column;
   the fluid port of a second of the ionization chambers is connected to a sample inlet; and
   a fluid outlet port of the second ionization chamber is connected to a pump.

9. The photoionization detector of claim 8, further comprising:
   a window transmissive of UV radiation, disposed between the first ionization chamber and the second ionization chamber;
   wherein:
   the first ionization chamber has a first side and a second side, the first side arranged proximate to the source UV radiation;
   the second ionization chamber is arranged proximate to the second side of the first ionization chamber; and
   the first ionization chamber and the second ionization chamber are arranged concentrically.

10. The photoionization detector of claim 9, wherein the window is removable.

11. The photoionization detector of claim 9, wherein the electrodes are arranged concentrically, and wherein the electrodes are further arranged such that the at least one electrode to which positively charged particles are attracted is substantially not exposed to the transmitted UV radiation.

12. A photoionization detector, comprising
   a plurality of ionization chambers, each of the ionization chambers comprising at least one fluid inlet port, at least one fluid outlet port, at least two electrodes arranged to generate an electric field to attract positively charged particles to at least one of the electrodes; and
   a source of high-energy photons arranged to transmit high-energy photoionization detector operates within an ambient environment, and wherein each of the ionization chambers is sealed in substantially gas-tight arrangement from others of the ionization chambers and from the ambient environment.

13. A photoionization detector, comprising:
   a plurality of ionization chambers, each of the ionization chambers comprising at least one fluid inlet port, at least one fluid outlet port, and at least two electrodes arranged to generate an electric field to attract positively charged particles to at least one of the electrodes; and
   a source of high-energy photons arranged to transmit high-energy photons into each the ionization chambers, wherein the electrodes are arranged concentrically, and wherein the electrodes are arranged such that the electric field is parallel to the direction of propagation of the high energy photons.

* * * * *